(12) United States Patent
Saltzman et al.

(10) Patent No.: US 7,963,996 B2
(45) Date of Patent: Jun. 21, 2011

(54) ANKLE PROSTHESIS METHODS

(75) Inventors: Charles L. Saltzman, Salt Lake City, UT (US); Albert H. Burstein, Sarasota, FL (US); Jonathan T. Deland, New York, NY (US)

(73) Assignees: University of Iowa Research Foundation, Iowa City, IA (US); Albert H. Bernstein, Sarasota, FL (US); Jonathan T. Deland, New York, NY (US)

( * ) Notice: Subject to any disclaimer, the term of this patent is extended or adjusted under 35 U.S.C. 154(b) by 0 days.

(21) Appl. No.: 12/628,556

(22) Filed: Dec. 1, 2009

(65) Prior Publication Data

US 2010/0305572 A1   Dec. 2, 2010

Related U.S. Application Data

(62) Division of application No. 10/965,070, filed on Oct. 14, 2004, now Pat. No. 7,625,409.

(60) Provisional application No. 60/510,887, filed on Oct. 14, 2003.

(51) Int. Cl.
   *A61F 2/42*   (2006.01)

(52) U.S. Cl. .................................................. 623/21.18

(58) Field of Classification Search ............... 623/21.18, 623/21.19, 21.11, 21.12, 20.31, 20.14, 20.15, 623/20.11, 17.11, 17.15
See application file for complete search history.

(56) References Cited

U.S. PATENT DOCUMENTS

| | | | |
|---|---|---|---|
| 3,872,519 A | 3/1975 | Giannestras et al. |
| 3,975,778 A | 8/1976 | Newton, III |
| 3,987,500 A | 10/1976 | Schlein |
| D242,957 S | 1/1977 | Treace |
| 4,021,864 A | 5/1977 | Waugh |
| 4,069,518 A | 1/1978 | Groth, Jr. et al. |
| 4,156,944 A | 6/1979 | Schreiber et al. |
| 4,166,292 A | 9/1979 | Bokros |
| 4,242,758 A | 1/1981 | Amis et al. |
| 4,309,778 A | 1/1982 | Buechel et al. |
| 4,340,978 A | 7/1982 | Buechel et al. |
| 4,360,931 A | 11/1982 | Hampton |
| 4,442,554 A | 4/1984 | Copes |
| 4,470,158 A | 9/1984 | Pappas et al. |
| 4,659,331 A | 4/1987 | Matthews et al. |
| 4,755,185 A | 7/1988 | Tarr |
| 4,778,473 A | 10/1988 | Matthews et al. |
| 5,019,109 A | 5/1991 | Voisin |
| 5,156,630 A | 10/1992 | Rappoport et al. |
| 5,312,216 A | 5/1994 | Hogg |
| 5,326,365 A | 7/1994 | Alvine |

(Continued)

FOREIGN PATENT DOCUMENTS

DE   3904004 A1   8/1990

(Continued)

OTHER PUBLICATIONS

Agility Total Ankle System Brochure—10 pages.

(Continued)

*Primary Examiner* — Alvin J Stewart

(74) *Attorney, Agent, or Firm* — Scott E. Kamholz; Foley Hoag LLP

(57) ABSTRACT

Methods of implanting an ankle prosthesis in a subject having an ankle joint in need of replacement.

4 Claims, 13 Drawing Sheets

U.S. PATENT DOCUMENTS

| | | | |
|---|---|---|---|
| 5,728,177 A | 3/1998 | Phillips | |
| 5,766,259 A | 6/1998 | Sammarco | |
| 5,800,564 A | 9/1998 | Gelineau | |
| 5,824,106 A | 10/1998 | Fournol | |
| 5,957,981 A | 9/1999 | Gramnas | |
| 6,039,763 A | 3/2000 | Shelokov | |
| 6,183,519 B1 | 2/2001 | Bonnin et al. | |
| 6,409,767 B1 | 6/2002 | Perice et al. | |
| 6,610,093 B1 | 8/2003 | Pisharodi | |
| 6,749,635 B1 | 6/2004 | Bryan | |
| 6,890,357 B2 | 5/2005 | Tornier | |
| 6,926,739 B1* | 8/2005 | O'Connor et al. | 623/21.18 |
| 6,939,380 B2 | 9/2005 | Guzman | |
| 6,994,727 B2 | 2/2006 | Khandkar et al. | |
| 6,997,954 B2 | 2/2006 | Zubok et al. | |
| 7,025,790 B2 | 4/2006 | Parks et al. | |
| 7,238,190 B2 | 7/2007 | Schon et al. | |
| 7,481,840 B2 | 1/2009 | Zucherman et al. | |
| 7,534,270 B2 | 5/2009 | Ball | |
| 7,625,409 B2* | 12/2009 | Saltzman et al. | 623/21.18 |
| 2003/0181985 A1 | 9/2003 | Keller et al. | |
| 2004/0002768 A1 | 1/2004 | Parks et al. | |
| 2004/0024462 A1 | 2/2004 | Ferree et al. | |
| 2004/0030399 A1 | 2/2004 | Asencio | |
| 2004/0138749 A1 | 7/2004 | Zucherman et al. | |
| 2004/0186585 A1 | 9/2004 | Feiwell | |
| 2005/0004676 A1 | 1/2005 | Schon et al. | |
| 2005/0049711 A1 | 3/2005 | Ball | |
| 2005/0125069 A1* | 6/2005 | Naegerl et al. | 623/21.18 |
| 2005/0182492 A1 | 8/2005 | Pappas et al. | |
| 2005/0192673 A1* | 9/2005 | Saltzman et al. | 623/21.18 |
| 2005/0256579 A1 | 11/2005 | Keller et al. | |
| 2006/0020345 A1 | 1/2006 | O'Connor et al. | |
| 2006/0142870 A1* | 6/2006 | Robinson et al. | 623/21.18 |
| 2006/0247788 A1* | 11/2006 | Ross | 623/21.18 |
| 2007/0027547 A1* | 2/2007 | Rydell et al. | 623/21.18 |
| 2007/0112431 A1* | 5/2007 | Kofoed | 623/21.18 |
| 2007/0173947 A1 | 7/2007 | Ratron et al. | |
| 2008/0097617 A1* | 4/2008 | Fellinger et al. | 623/21.18 |
| 2009/0054992 A1 | 2/2009 | Landes et al. | |
| 2009/0082875 A1* | 3/2009 | Long | 623/21.18 |
| 2009/0182433 A1 | 7/2009 | Reiley et al. | |
| 2010/0057216 A1* | 3/2010 | Gannoe et al. | 623/21.18 |
| 2010/0280625 A1* | 11/2010 | Sanders et al. | 623/21.18 |
| 2010/0318088 A1* | 12/2010 | Warne et al. | 606/87 |

FOREIGN PATENT DOCUMENTS

| | | |
|---|---|---|
| DE | 10123124 C1 | 12/2002 |
| FR | 2724108 A1 | 3/1996 |

OTHER PUBLICATIONS

FDA Executive Summary Brochure—57 pages.

Mayo Clinic-Ankle replacement. Clinical trial extended for STAR ankle replacement device; Jul. 2003, found at http://www.mayoclinic.org/checkup-2003/july-ankle.html.

Murnaghan et al. "Total ankle replacement. Early Experiences with STAR prosthesis," The Ulster Medical Journal, vol. 74, No. 1, pp. 9-13, May 2005.

Pyevich et al., "The Total Ankle Arthroplasty: a Unique Design. Two to Twelve-Year Follow-up," J. Bone Joint Surg Am. 1998;80:1410-20.

Talaris Anatomic Ankle Brochure, Jul. 2006—6 pages.

Talaris Anatomic Ankle Brochure, Excerpt of, Jul. 2006—2 pages.

International Search Report (PCT/US04/33913).

* cited by examiner

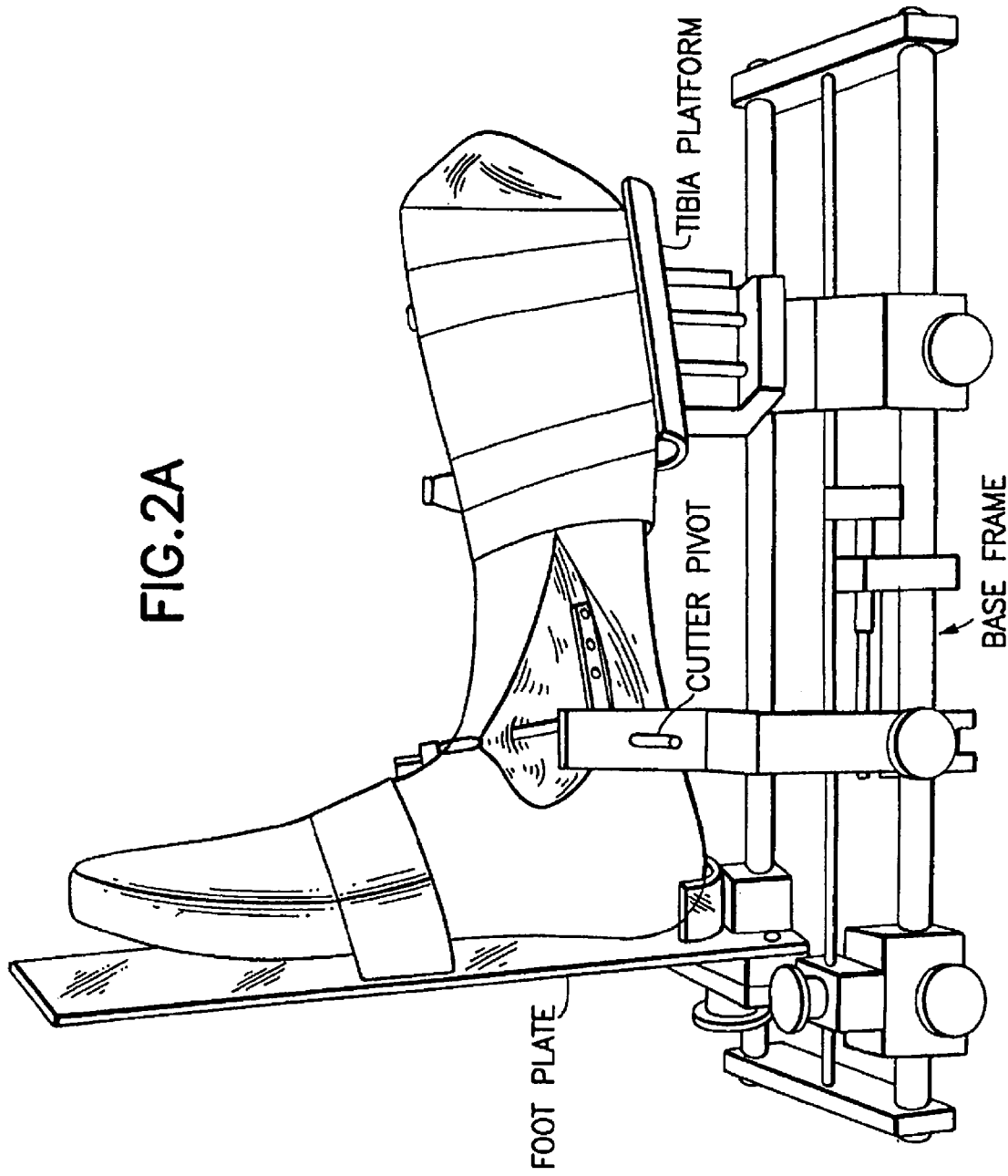

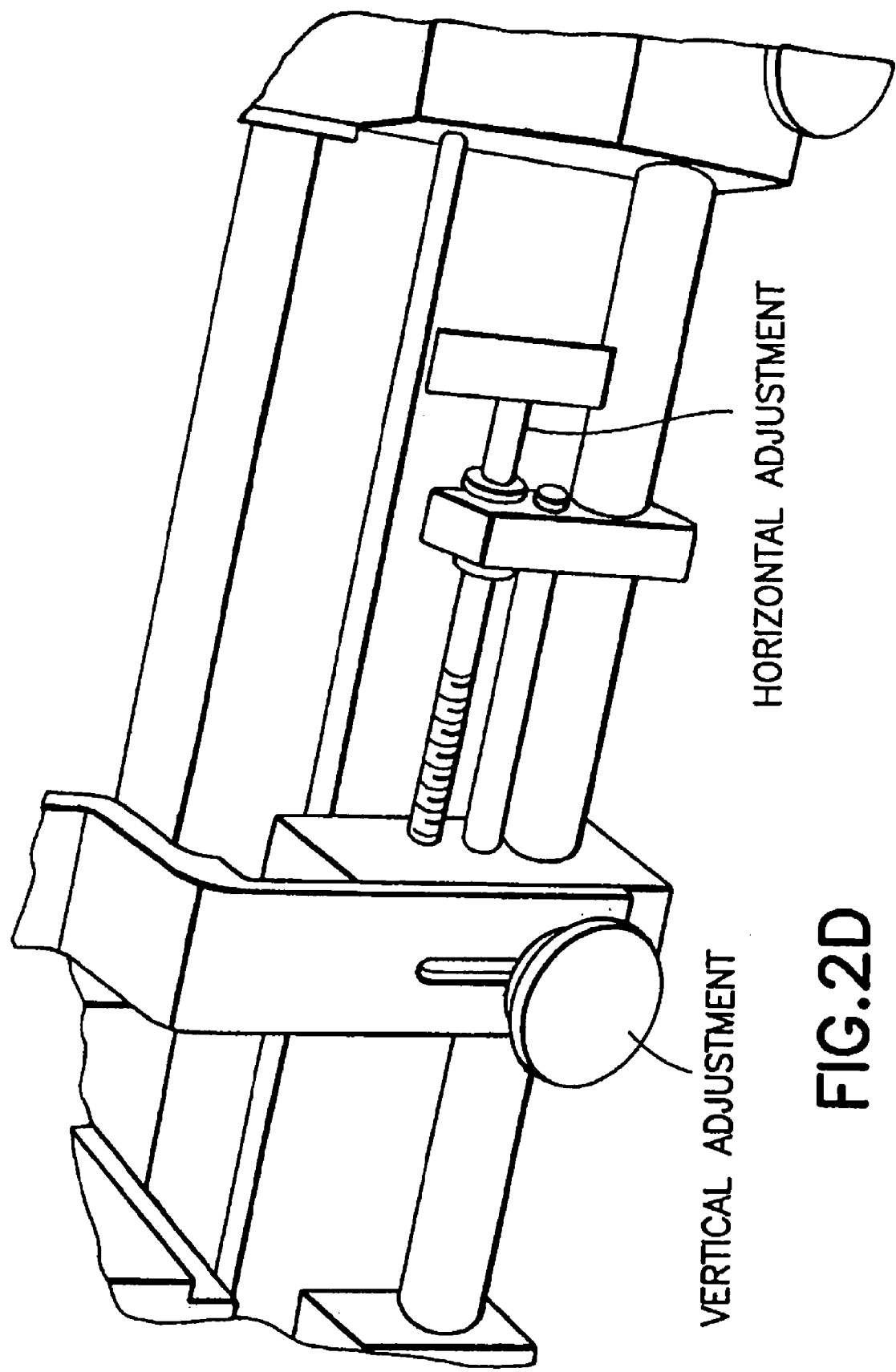

ANKLE PROSTHESIS METHODS

CROSS-REFERENCE TO RELATED APPLICATION

This application is a division of U.S. application Ser. No. 10/965,070, filed Oct. 14, 2004, which claims the benefit of U.S. Provisional Application Ser. No. 60/510,887, filed Oct. 14, 2003, which is hereby incorporated herein by reference.

FIELD

One embodiment of the present invention relates to an ankle prosthesis.

Another embodiment of the present invention relates to a total ankle replacement prosthesis.

Another embodiment of the present invention relates to an ankle replacement (partial or total) which is adapted, for example: (a) to treat arthritis of the ankle (e.g., ankle arthritis of any cause: after previous trauma; primary; malalignment induced; after hindfoot fusion; from recurrent ankle instability; rheumatoid or inflammatory arthritis; gout; local growth; dysplasia; growth plate arrest; avascular necrosis; hemophilia; distant septic event); (b) to revise a fused ankle; and/or (c) to treat trauma. The ankle replacement may be carried out by replacing one or more joint surfaces of an ankle joint.

Another embodiment of the present invention relates to a method for inserting an ankle prosthesis.

BACKGROUND

In the search for a workable ankle arthroplasty, various designs have been tried. As seen below in Table 1, certain published results relating to conventional total ankle arthroplasty were disappointing for both patients and surgeons (the typical clinical series of Table 1 includes 20-40 patients followed for an average of five years or less; only general observations can be made from this data).

TABLE 1

Good-to-Excellent Satisfaction Rates After Total Ankle Replacements - Conventional Designs

| Device | Author/Year | # of Ankles | Avg F/U (months) | Satisfaction Rate |
|---|---|---|---|---|
| Smith | Dini/80 | 21 | 27 | 46% |
| ICLH | Goldie/82 | 18 | 36 | 60% |
| TPR | Jensen/92 | 23 | 59 | 69% |
| Bath & Wessex | Carlsson/93 | 52 | 60 | 81% |
| TPR | Kumar/88 | 37 | 60 | 52% |
| LCS | Buechel/92 | 40 | 72 | 85% |
| Smith | Kirkup/85 | 18 | 84 | 61% |
| Mayo | Kitaoka/96 | 160 | 108 | 19% |

As Table 1 reveals, patient satisfaction with conventional, cemented ankle implants has ranged from 19 percent to 85 percent (see, e.g., Dini A A, Bassett F H: Evaluation of the early result of Smith total ankle replacement. *Clin Orthop* 1980; 146:228-230; Goldie I F, Herberts P: Prosthetic replacement of the ankle joint. *Reconstr Surg and Traumat* 1981; 18:205-210; Jensen N C, Kroner K: Total ankle joint replacement: A clinical follow-up. *Orthopedics* 1992; 15:236-240; Carlsson A S, Henricson A, Linder L, Nilsson J A, Redlund-Johneur: A survival analysis of 52 Bath-Wessex ankle replacements. *The Foot* 1994; 4:34-40; Kumar D J R: Total ankle arthroplasty. A review of 37 cases. *J Tn Med Assoc* 1988; 81:682-685; Buechel F F, Pappas M, Iorio U: N J low contact stress total ankle replacement: Biomechanical rationale and review of 23 cementless cases. *Foot Ankle* 1988; 8:270-290; Kirkup J: Richard Smith ankle arthroplasty. *J Roy Soc Med* 1985; 78:301-304; Kitaoka H B, Patzer G L: Clinical results of the Mayo total ankle arthroplasty. *J Bone Joint Surg* 1996; 78A: 1658-1664).

It is believed that length of follow-up was a major factor with patient satisfaction, as patients with longer follow-ups generally had declining degrees of satisfaction. As seen below in Table 2, the rates of radiographic loosening with these conventional implants were quite substantial, ranging from 22 percent to 75 percent (see, e.g., Goldie I F, Herberts P: Prosthetic replacement of the ankle joint. *Reconstr Surg and Traumat* 1981; 18:205-210; Jensen N C, Kroner K: Total ankle joint replacement: A clinical follow-up. *Orthopedics* 1992; 15:236-240; Carlsson A S, Henricson A, Linder L, Nilsson J A, Redlund-Johneur: A survival analysis of 52 Bath-Wessex ankle replacements. *The Foot* 1994; 4:34-40; Kumar D J R: Total ankle arthroplasty. A review of 37 cases. *J Tn Med Assoc* 1988; 81:682-685; Kirkup J: Richard Smith ankle arthroplasty. *J Roy Soc Med* 1985; 78:301-304; Kitaoka H B, Patzer G L: Clinical results of the Mayo total ankle arthroplasty. *J Bone Joint Surg* 1996; 78A: 1658-1664; Helm R, Stevens J: Long-term results of total ankle replacement. *J Arthroplasty* 1986; 1:271-277; Bolton-Maggs B G, Sudlow R A, Freeman MAR: Total ankle arthroplasty. A long-term review of the London Hospital experience. *J Bone Joint Surg* 1985; 67B: 785-790). Of note, it is believed that some of the major factors implicated with loosening were: 1) highly constrained designs; and 2) cement fixation (it might have been the use of cement alone, or the combination of the use of cement to create adequate space for cementation, which was a major contributing factor to increased loosening rates).

TABLE 2

Radiographic Loosening After Total Ankle Replacement - Conventional Designs

| Device | Author/Year | # of Ankles | Avg. F/U (months) | Loosening Rate |
|---|---|---|---|---|
| ICLH | Goldie/82 | 18 | 36 | 22% |
| ICLH | Helm/86 | 14 | 54 | 57% |
| TPR | Jensen/92 | 23 | 59 | 52% |
| Bath & Wessex | Carlsson/93 | 52 | 60 | 67% |
| TPR | Kumar/88 | 37 | 60 | 26% |
| ICLH | Bolton-Maggs/85 | 41 | 66 | 32% |
| Smith | Kirkup/85 | 18 | 84 | 39% |
| Mayo | Kitaoka/96 | 160 | 108 | 75% |

Further, conventional total ankle arthroplasty has also been plagued with unusually high wound problems. The soft tissues around the ankle region, especially in rheumatoid and elderly patients, provide a relatively thin envelope for arthroplasty containment. Problems with superficial and deep infections, resection arthroplasties, attempted re-implantations or arthrodeses and, occasionally, below-knee amputations have dampened the enthusiasm of many orthopaedic surgeons involved with conventional total ankle replacement. In this regard, see Table 3 below, relating to published "long-term" results after conventional ankle arthrodesis.

TABLE 3

Published "Long-Term" Results After
Conventional Ankle Arthrodesis

| Author/<br>Year | # of<br>Patients | Avg<br>F/U<br>(years) | Major **<br>Complications | Continued<br>Pain | Hindfoot<br>DJD |
|---|---|---|---|---|---|
| Said/78 | 36 | 8 | 24% | * | >50% |
| Mazur/79 | 12 | 8 | * | 25% | 100% |
| Morrey/80 | 41 | 8 | 48% | 76% | 50% |
| Ahlberg/81 | 41 | 12 | 32% | 68% | 44% |
| Boobyer/81 | 58 | 9 | 21% | * | * |
| Morgan/85 | 101 | 10 | 10% | * | * |
| Lynch/88 | 62 | 7 | 34% | * | * |
| Glick/96 | 34 | 8 | 6% | * | * |

While somewhat better short term results associated with conventional implants have stimulated interest in total ankle replacement, such conventional implants have shown their deficiencies. For example, one conventional prosthesis (the AGILITY ankle replacement) has shown an overall high rate of satisfaction in early follow up but with evident problems (see, e.g., Pyevich M T, Saltzman C L, Callaghan J J, Alvine F G: Total ankle arthroplasty: A unique design. Two to twelve-year follow-up. *J. Bone Joint Surg., Vol* 80-A(10): 1410-1420, October, 1998; Saltzman C L, Moss T, Brown T D, Buckwalter J A Total Ankle Replacement Revisited. JOSPT 30(2):56-67, February, 2000; Saltzman C L, Alvine F G, Sanders R W, Gall RJ. Challenges with Initial Use of a Total Ankle. Clinical Orthopaedics and Related Research (Accepted)).

One issue in this regard is the large amount of bone that is typically resected during conventional surgery. This creates a problem if revision is required because the subsequent lack of bone makes revision or conversion to a fusion problematic. The difficulties caused by having to resect a large amount of bone will become more apparent over time as with longer follow up the need for revision becomes more common.

Another issue with this conventional AGILITY ankle replacement is the limited range of motion it allows after surgery. It is believed that in approximately fifty percent of the cases the patient's plantarflexion contracture remained with patients not being able to dorsiflex significantly beyond neutral position.

A second conventional prosthesis (the STAR), while believed to not require as much bone resection, has articular contact surfaces that are flat in the medial-lateral direction, thus making edge loading necessary when resisting the varus/valgus loads imposed upon the ankle during ordinary ambulation (see, e.g., Kofoed H, Danborg L: Biological fixation of ankle arthroplasty. *Foot* 1995; 5:27-3 1; Kofoed H, Toben S: Ankle arthroplasty for rheumatoid arthritis and osteoarthritis: Prospective long-term study of cemented replacements. *J Bone Joint Surg* 1998; 80B:328-332).

Further still, additional papers include the following: Morgan C D, Henke J A, Bailey R W, Kaufer H: Long-term results of tibiotalar arthrodesis. *J Bone Joint Surg* 1985; 7A:546-550; Glick T M, Morgan D D, Myerson M S, Sampson T O, Mann J A: Ankle arthrodesis using an arthroscopic method: Long-term follow-up of 34 cases. *Arthroscopy* 1996; 12:428-434; Money B F, Wiedeman G P: Complications in long-term results of ankle arthrodeses following trauma. *J Bone Joint Surg* 1980; 62A:777-784; Ahlberg A, Henricson A S: Late results of ankle fusion. Acta Orthop Scand 1981; 52:103-105; Mazur J M, Schwartz E, Simon S R: Ankle arthrodesis; long-term follow-up with gait analysis. *J Bone Joint Surg* 1979; 61A:964-975; Boobbyer G N: The long-term results of ankle arthrodesis. Acta Orthop Scand 1981; 52:107-110; Said B, Hunka L, Siller T N: Where ankle fusion stands today. *J Bone Joint Surg* 1978; 60B:211-214; Lynch A F, Bourne R B, Rorabeck C H: The long-term results of ankle arthrodesis. *J Bone Joint Surg* 1988; 70B:113-116.

Moreover, issued patents include the following: U.S. Pat. No. 6,183,519, entitled Ankle Prosthesis; U.S. Pat. No. 5,957,981, entitled Adjustable Prosthesis Joint; U.S. Pat. No. 5,824,106, entitled Ankle Prosthesis; U.S. Pat. No. 5,800,564, entitled Ankle Prosthesis With Angle Adjustment; U.S. Pat. No. 5,766,259, entitled Total Ankle Prosthesis And Method; U.S. Pat. No. 5,728,177, entitled Prosthesis With Foam Block Ankle; U.S. Pat. No. 5,312,216, entitled Artificial Joint Prosthesis; U.S. Pat. No. 5,156,630, entitled Ankle Joint Prosthesis Fixable In More Than One Orientation; U.S. Pat. No. 5,019,109, entitled Multi-Axial Rotation System For Artificial Ankle; U.S. Pat. No. 4,778,473, entitled Prosthesis Interface Surface And Method Of Implanting; U.S. Pat. No. 4,755,185, entitled Prosthetic Joint; U.S. Pat. No. 4,659,331, entitled Prosthesis Interface Surface And Method Of Implanting; U.S. Pat. No. 4,470,158, entitled Joint Endoprosthesis; U.S. Pat. No. 4,442,554, entitled Biomechanical Ankle Device; U.S. Pat. No. 4,360,931, entitled Prosthetic Ankle; U.S. Pat. No. 4,340,978, entitled New Jersey Meniscal Bearing Knee Replacement; U.S. Pat. No. 4,309,778, entitled New Jersey Meniscal Bearing Knee Replacement; U.S. Pat. No. 4,166,292, entitled Stressed Reinforced Artificial Joint Prosthesis; U.S. Pat. No. 4,156,944, entitled Total Ankle Prosthesis; U.S. Pat. No. 4,069,518, entitled Total Ankle Prosthesis; U.S. Pat. No. 4,021,864, entitled Ankle Prosthesis; U.S. Pat. No. D242,957, entitled Total Ankle Prosthesis; U.S. Pat. No. 3,987,500, entitled Surgically Implantable Total Ankle Prosthesis; and U.S. Pat. No. 3,975,778, entitled Total Ankle Arthroplasty.

BRIEF DESCRIPTION OF THE DRAWINGS

FIGS. 2A-2K show implantation of an ankle prosthesis according to an embodiment of the present invention.

Figure 1A:
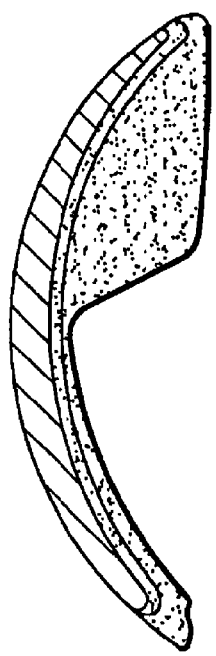
FIGS. 1A-1E show an ankle prosthesis according to an embodiment of the present invention.

Among those benefits and improvements that have been disclosed, other objects and advantages of this invention will become apparent from the following description taken in conjunction with the accompanying figures. The figures constitute a part of this specification and include an illustrative embodiment of the present invention and illustrate various objects and features thereof.

SUMMARY

In an embodiment, a fixed-bearing ankle prosthesis includes a tibial component for attachment to a tibia, wherein the tibial component has first and second surfaces, and a talar component for attachment to a talus, wherein the talar component has first and second surfaces and medial and lateral edges. At least a portion of the first surface of the tibial component is configured to be disposed adjacent the tibia. At least a portion of the first surface of the talar component is configured to be disposed adjacent the talus. At least a portion of the second surface of the tibial component and at least a portion of the second surface of the talar component contact one another directly to form an articulation interface between the tibial component and the talar component. The articulation interface includes a bicondylar geometry such that the second surface of the tibial component defines a medial condylar facet and a lateral condylar facet and the second surface of the talar component includes a medial condyle and a lateral condyle. The medial and lateral condylar facets of the tibial component have concave circular arc cross-sections extending in a medial-lateral plane. The medial condyle of the talar component has a first single radius in the medial-lateral plane that defines a convex circular arc cross-section continuously extending, in the medial-lateral plane, from the medial edge of the talar component to a concave central portion of the talar component second surface separating the medial and lateral condyles. The lateral condyle of the talar component has a second single radius in the medial-lateral plane that defines a convex circular arc cross-section continuously extending, in the medial-lateral plane, from the lateral edge of the talar component to the concave central portion of the talar component second surface. The concave circular arc cross-section of the medial condylar facet of the tibial component has a radius in the medial-lateral plane larger than the first radius. The concave circular arc cross-section of the lateral condylar facet of the tibial component has a radius in the medial-lateral plane larger than the second radius.

In another embodiment, a fixed-bearing ankle prosthesis includes a tibial component and a talar component. The tibial component includes a tibial attachment surface and a tibial articulating surface. The talar component includes a medial edge, a lateral edge, a talar attachment surface, and a talar articulating surface, the talar articulating surface directly contacting the tibial articulating surface. The tibial articulating surface includes a medial concave condylar facet and a lateral concave condylar facet, each condylar facet having a radius of curvature in a medial-lateral plane that defines a respective circle arc, the facets separated from one another by a convex central portion. The talar articulating surface includes a medial convex condyle that underlies the medial condylar facet, and a lateral convex condyle that underlies the lateral condylar facet. The condyles are separated from one another by a concave central portion that underlies the tibial convex central portion. The medial condyle of the talar component has a first single radius of curvature in the medial-lateral plane that defines a convex circular arc cross-section continuously extending, in the medial-lateral plane, from the medial edge of the talar component to the concave central portion of the talar articulating surface. The lateral condyle of the talar component has a second single radius of curvature in the medial-lateral plane that defines a convex circular arc cross-section continuously extending, in the medial-lateral plane, from the lateral edge of the talar component to the concave central portion of the talar component second surface. The medial condyle radius of curvature is smaller than the medial condylar facet radius of curvature, and the lateral condyle radius of curvature is smaller than the lateral condylar facet radius of curvature.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

In one embodiment an ankle prosthesis according to the present invention minimizes edge loading by using bicondylar articular geometry which enhances varus/valgus stability while maintaining an appropriately central load distribution within the prosthesis. In this regard, it is believed that in combination with adequate bone coverage of the resected bones by the prosthesis, an appropriately central load distribution would minimize prosthesis subsidence into the bone (by minimizing bone stress). Such a bicondylar geometry may allow the achievement of varus/valgus stability by shifting the joint compressive load center medially or laterally upon the joint contact surface, but prevents the joint compression load center from reaching the edge of the contact surface. An appropriate mechanism for varus/valgus stability may incorporate the shifting of the joint contact load from the medial to the lateral bicondylar surface for moderate varus/valgus loads and augmenting this stability mechanism with tensile loads in the collateral ligaments spanning the ankle joint. To produce collateral ligament loads, it may be necessary to stretch the ligaments and hence allow the opening of either the medial or the lateral condylar surfaces. By use of full radii of curvature of the medial and lateral bicondylar surfaces this embodiment may allow varus/valgus angulation to the extent of approximately, for example (which example is intended to be illustrative and not restrictive) three to five degrees, while maintaining essentially full central contact within either the medial or lateral condyle. This allows the required contact load shifting and stretching of the appropriate collateral ligament without significant edge loading. In another example (which example is intended to be illustrative and not restrictive), the angulation may be one to ten degrees.

In another embodiment an ankle prosthesis according to the present invention utilizes articular surface(s) with conical shape(s) which operate to couple the flexion/extension and inversion/eversion (it is believed that a contributing factor to a stable gait and proper foot/ground contact pattern is the coupling between the flexion/extension mechanism and the inversion/eversion motion normally present in the ankle joint).

In another embodiment an ankle prosthesis according to the present invention utilizes a design that: (a) in extreme dorsiflexion provides a maximized plantarflexion moment arm; and (b) in extreme plantarflexion provides a maximized dorsiflexion moment arm. This may be accomplished by choosing appropriate radii of curvature for one or more articular surfaces (e.g., so as to allow approximately, for example (which example is intended to be illustrative and not restrictive), two or three millimeters of anterior/posterior translation of the tibial and talar components). In another example (which example is intended to be illustrative and not restrictive), one to five millimeters of anterior/posterior translation of the tibial and talar components may be provided.

In another embodiment an ankle prosthesis utilizes a design that provides for the "contact point" or center of contact pressure to move anteriorly with dorsiflexion and posteriorly with plantarflexion (e.g., to achieve an acceptable range of motion by allowing the ankle joint to follow the biomechanical principle that, in extreme positions of motion, the muscle group with the more favorable moment arm is that group which opposes the extreme motion.

Of note, conventional ankle joint prostheses typically attempt to achieve low contact stress and low wear by using either fully congruent contact surfaces, such as found in mobile bearings, or so called flat-on-flat designs that provide cylindrical articulating surfaces. While various embodiments of the present invention provide the above described bicondylar geometry, the above described coupled flexion/extension and inversion/eversion motion and the above described anterior/posterior translation of the center of the joint contact surface, an additional embodiment combines these three features in such a way so as to avoid either fully congruent articular surfaces or line to line contact articular surfaces (i.e., an embodiment of the present invention utilizes articular surfaces that are not fully congruent in the anterior/posterior direction or the medial/lateral direction). More particularly, the surface geometry in this embodiment is comprised of circle arcs. These arcs form both the medial/lateral and anterior/posterior contours of the tibio-talar articulating surface. Moreover, in the medial/lateral direction, these radii overlie a conical section. In one example (which example is intended to be illustrative and not restrictive) a ratio of the talar component radii of curvature of both medial and lateral bicondylar surfaces, in the medial/lateral direction, may be between 92% and 96% of the corresponding tibial component radii of curvature of both medial and lateral bicondylar surfaces (i.e., the medial-lateral plane radii of the circular arc cross-sections of the tibial component are larger than corresponding radii of the circular arc cross-sections of the talar component). In another example (which example is intended to be illustrative and not restrictive) the corresponding ratios for these two articulating condylar surfaces in the anterior/posterior direction may be between 85% and 96% (i.e., the anterior-posterior radii of the circular arc cross-sections of the tibial component are larger than corresponding radii of the circular arc cross-sections of the talar component).

Of further note, an ankle joint is composed of three articulating surfaces: tibial/talar articulation, medial malleolus/talar articulation, and lateral malleolus/talar articulation. Conventional ankle prostheses typically do not allow the surgeon to choose, at the time of surgery, which of these three joint surfaces will be replaced (it is believed that some conventional prostheses provide only a hemiarthroplasty on the medial and lateral sides). This is a potential source of impingement or pain from articulation of the arthritic joint surface against the metal surface. While it is true that this is not necessarily a concern in all the patients, many of whom may have minimal arthritic changes in the medial or lateral gutters, it may be desirable to provide flexibility at the time of surgery according to an embodiment of the present invention (e.g., so that if the surgeon identifies arthritis in the medial or lateral gutter, a total joint replacement rather than hemiarthroplasty can be performed).

In another embodiment an ankle replacement, implant procedure, and implant instrumentation are provided which: 1) do not sacrifice too much bone (which excess sacrifice could make revision of the implant and/or conversion to a fusion difficult); 2) do not place the implant on relatively weak bone (which could encourage subsidence,); 3) do not allow excessive loosening of the implant from poor fixation; and 4) do not result in a significant incidence of wound problems.

In another embodiment an ankle prosthesis may include an element (e.g., a button with an articular surface (e.g., a spherical or spheroidal shaped articular surface)) that can be placed on either or both malleolar articulating surfaces to form an articular interface with lateral surfaces of the talar component (or any biomechanical axis). In one example (which example is intended to be illustrative and not restrictive), this feature may provide the surgical option of resurfacing one or both of the medial and lateral gutters (e.g., which lateral gutter may comprise a lateral fibula and talar articular surface)).

Referring now to FIGS. 1A-1E, an ankle prosthesis according to an embodiment of the present invention is shown.

FIG. 1A shows a side view of a talar component of the ankle prosthesis. The talar component has a concave first surface that is configured to be disposed adjacent the talus and a second surface which articulates with a tibial component.

Figure 1B:
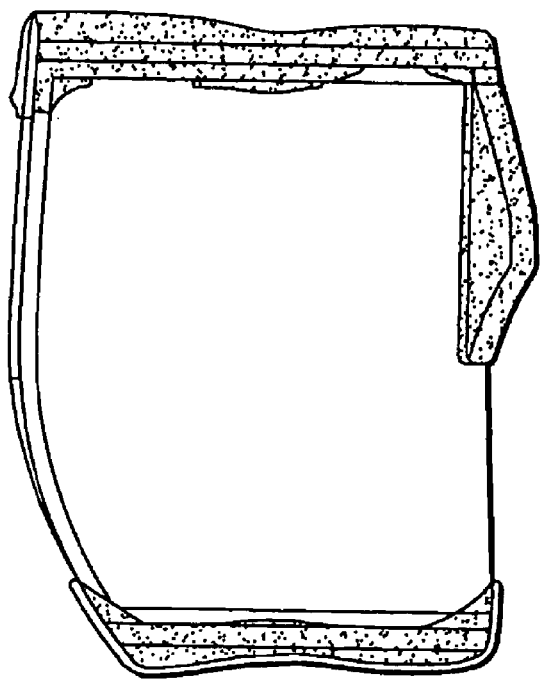

FIG. 1B shows a view of the talar component from its first surface.

Figure 1C:
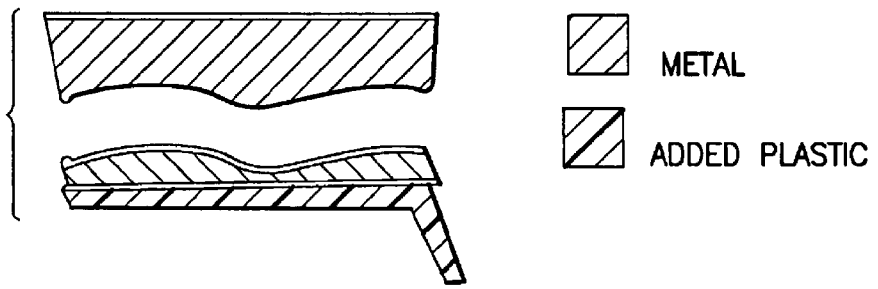

FIG. 1C shows a partial medial-lateral cross-section of the tibial (upper) and talar (lower) components. The central portion of the talar component second surface is concave, and a central portion of the tibial component second surface, which separates the medial and lateral condylar facets and which overlies the talar component central portion, is convex.

Figure 1E:
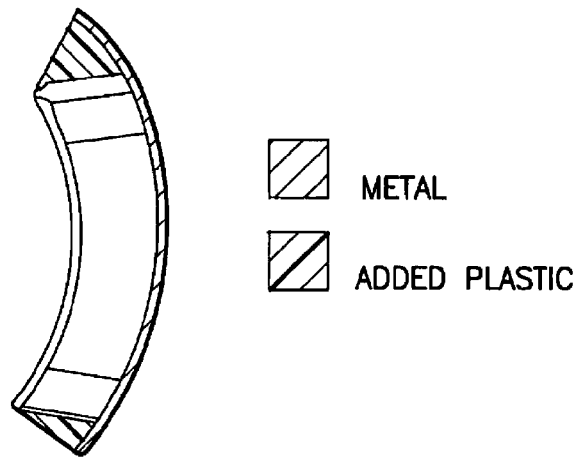
Figure 1D:
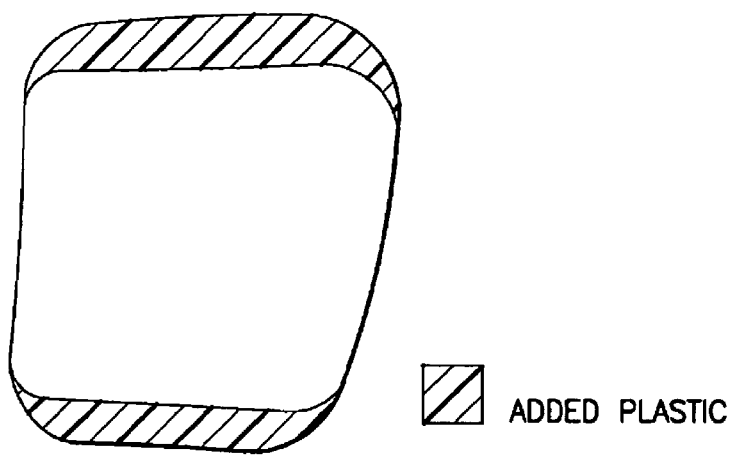
Figure 2B:
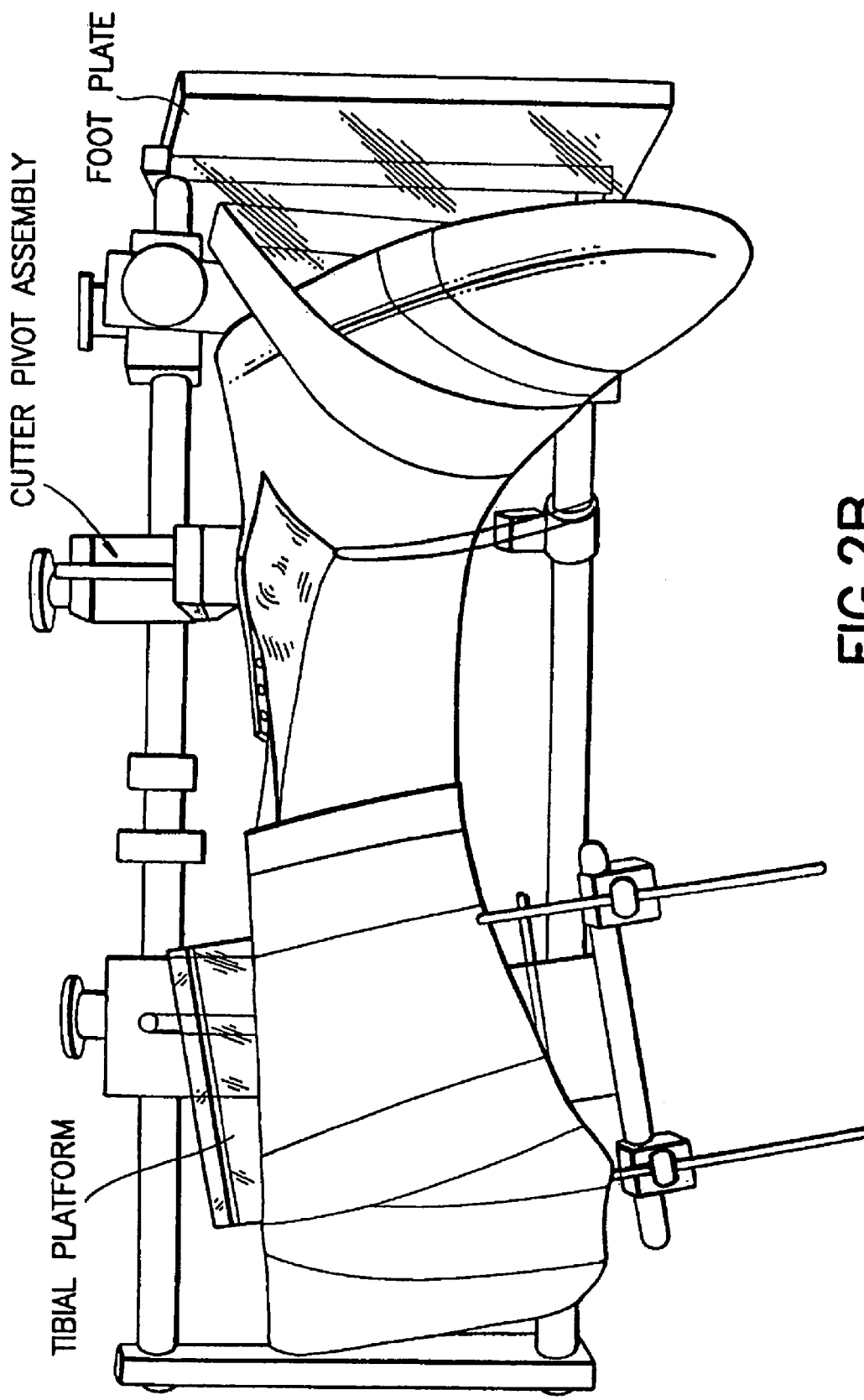
Figure 2C:
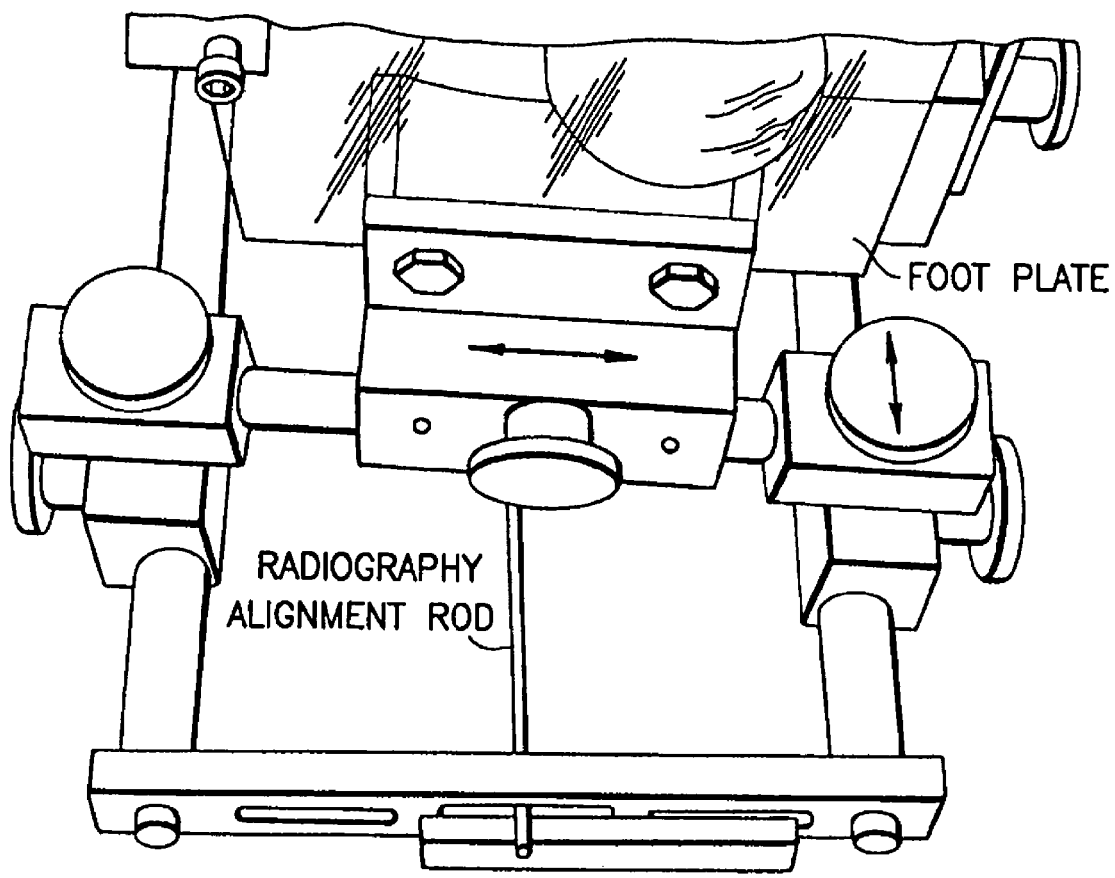
Figure 2E:
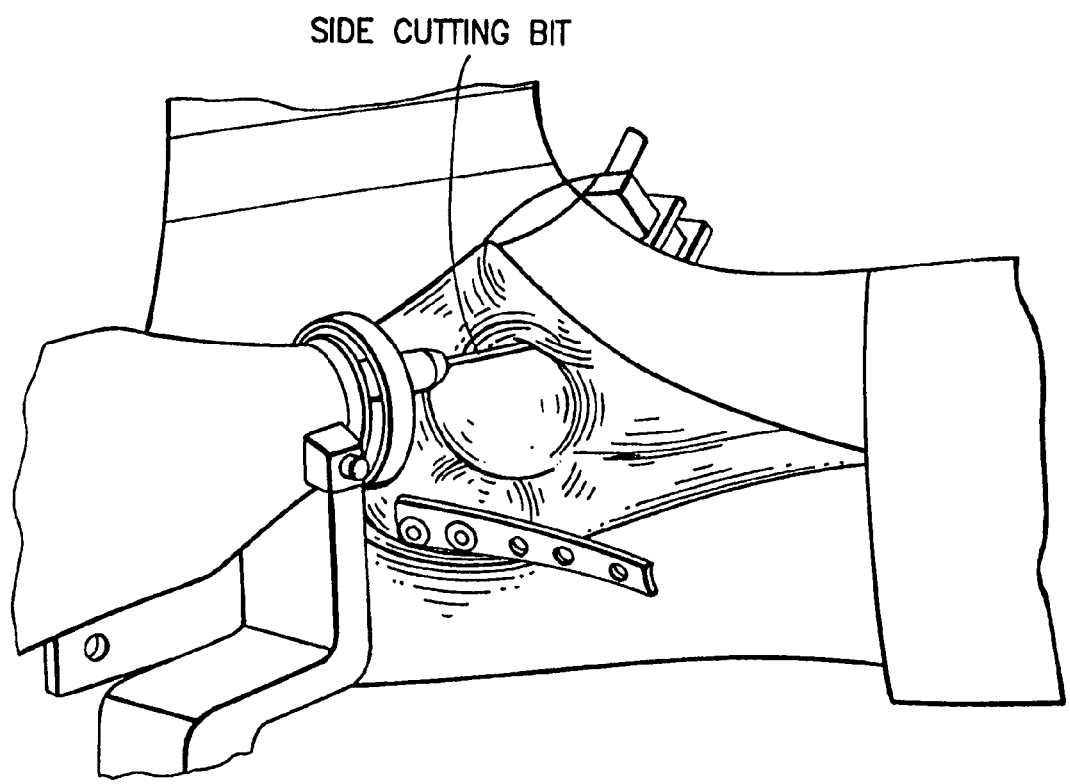
Figure 2F:
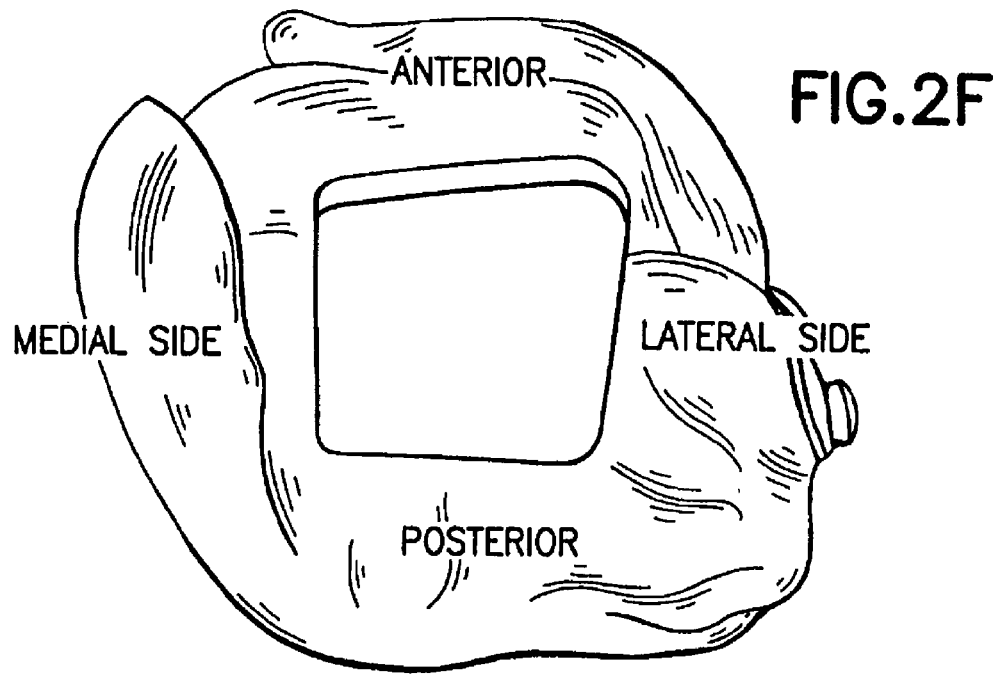
Figure 2G:
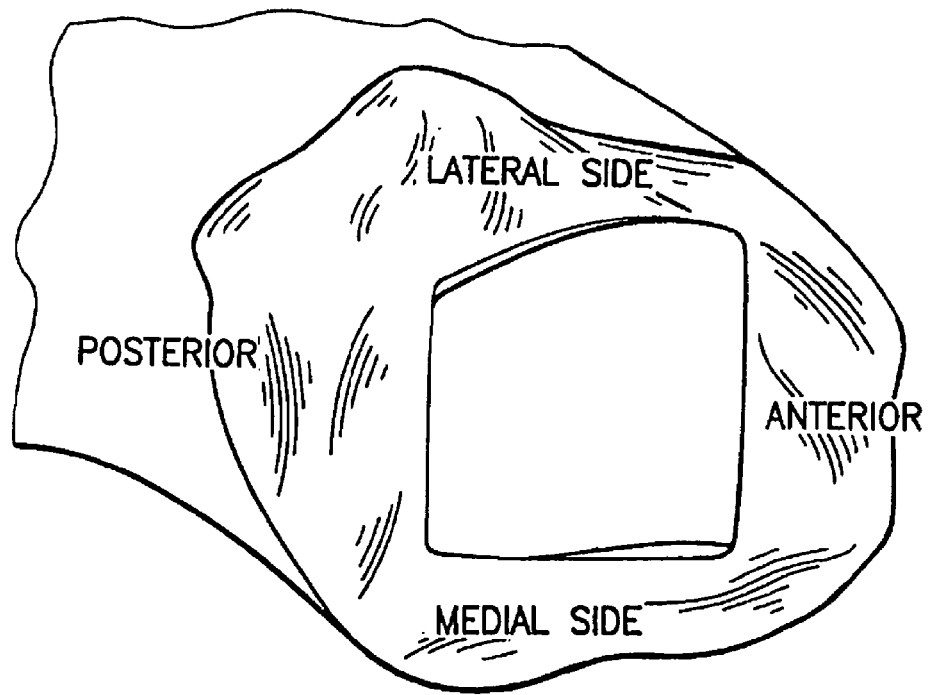
Figure 2H:
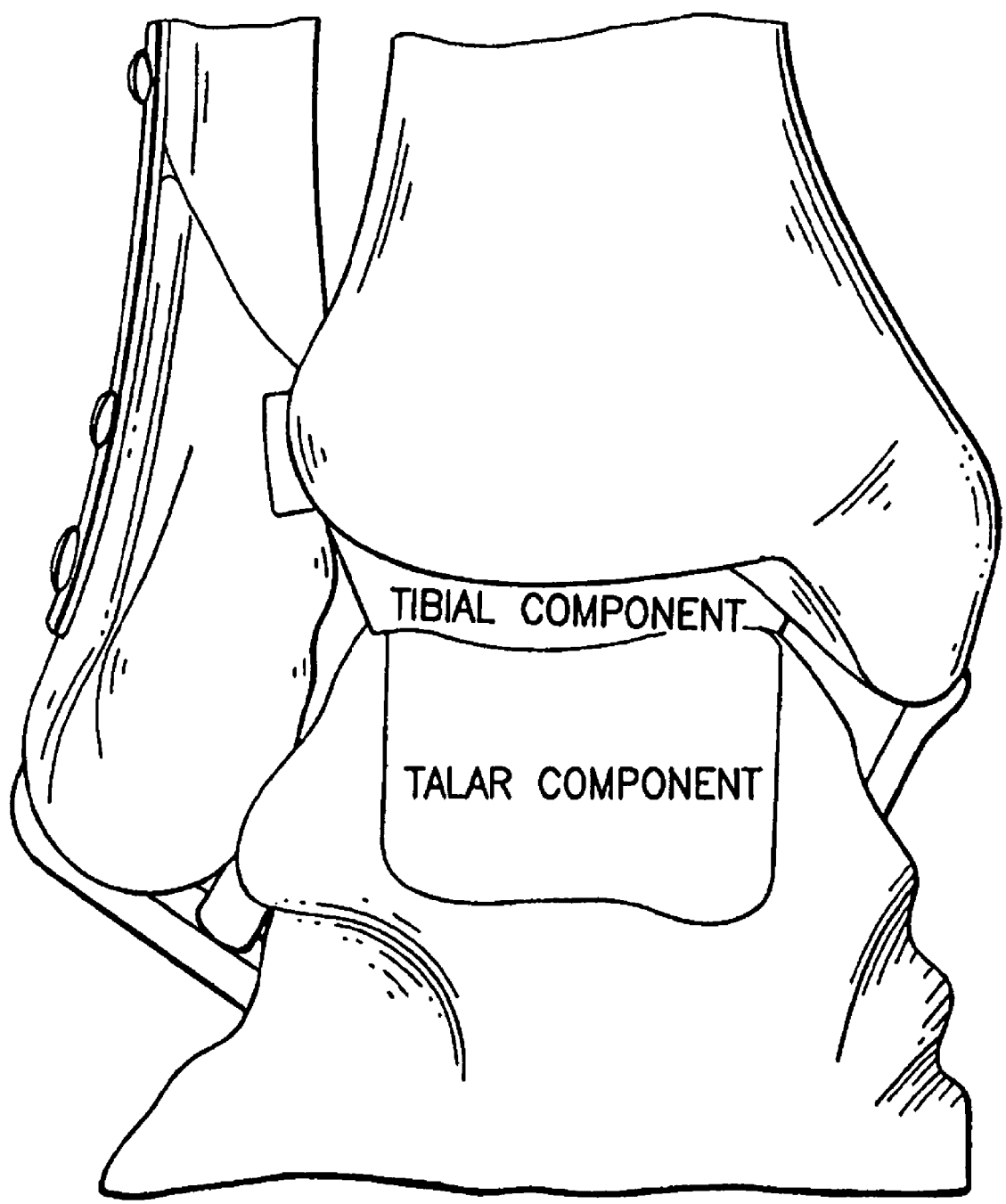
Figure 21:
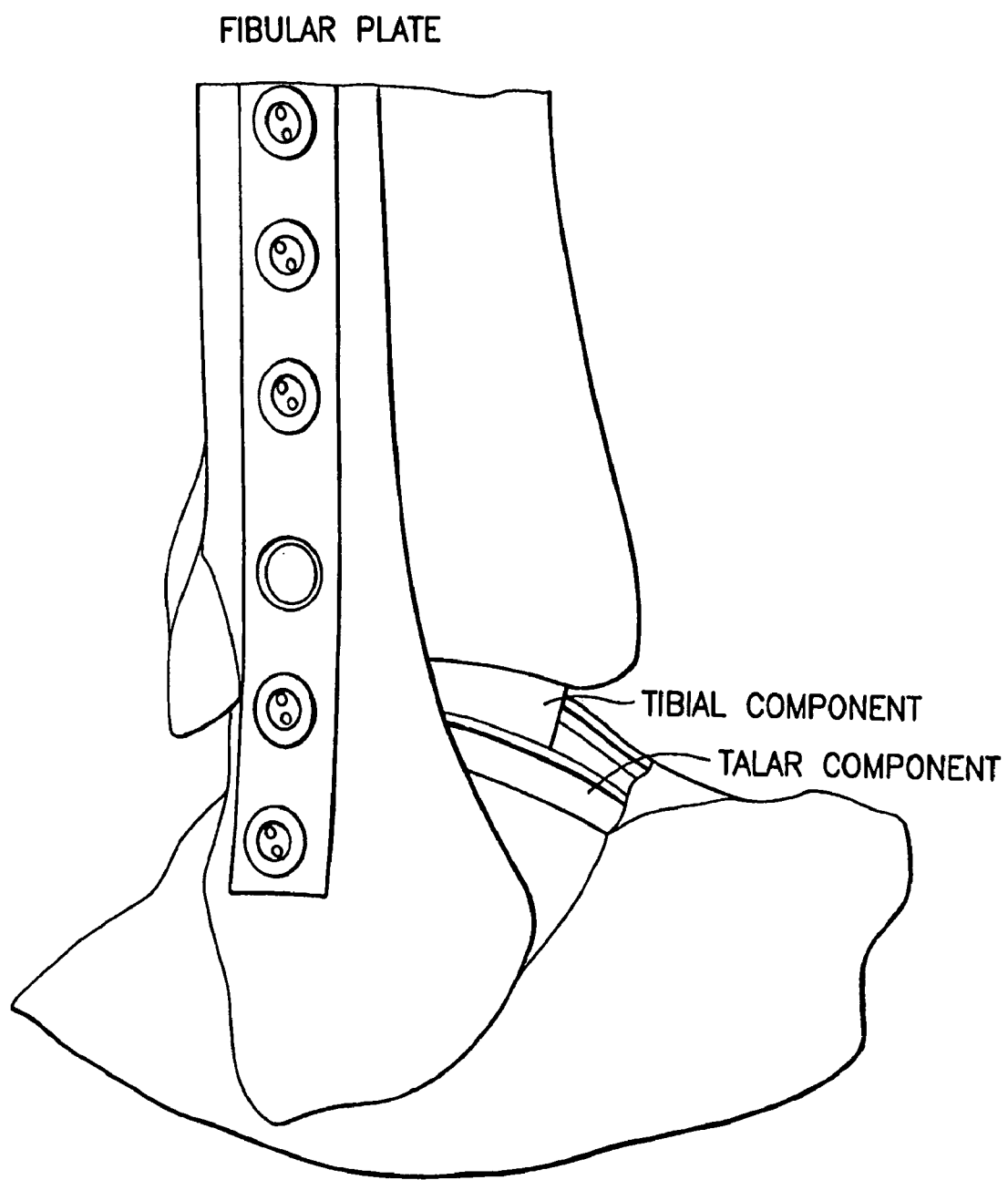
Figure 2J:
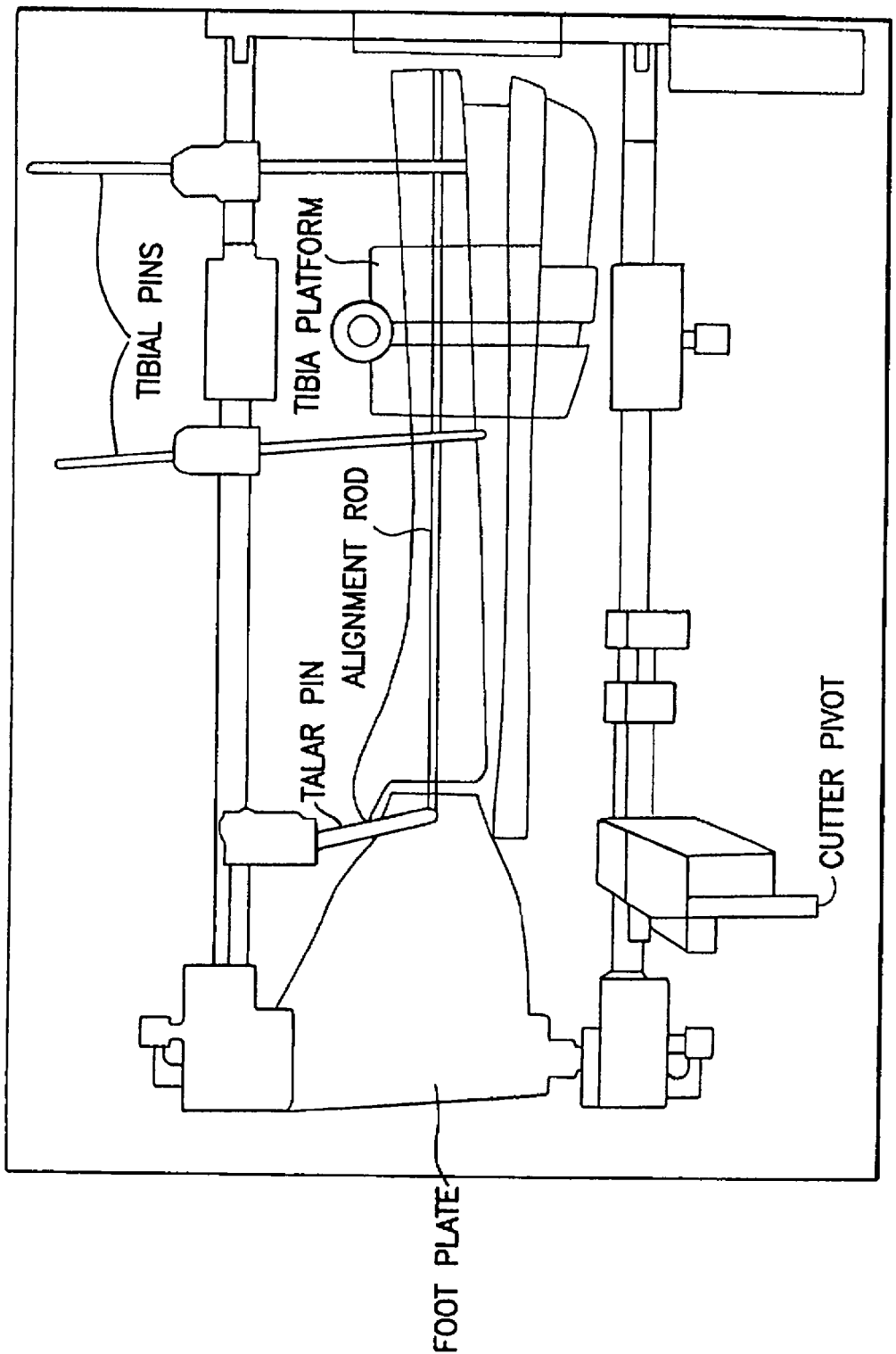
Figure 2K:
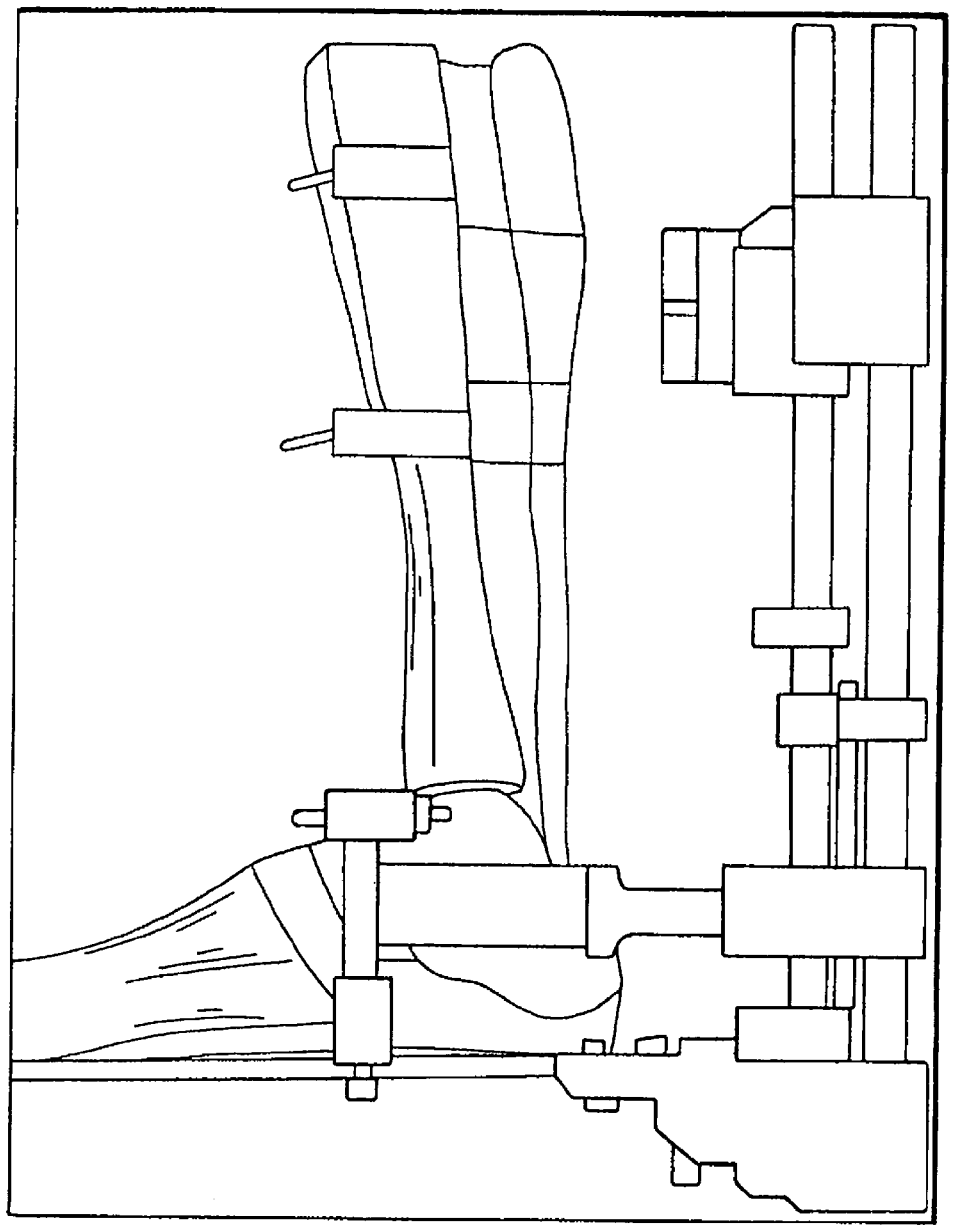

FIG. 1D shows a side view of a tibial component of the ankle prosthesis. The tibial component has a convex first surface that is configured to be disposed adjacent the tibia and a second surface which articulates with the talar component.

FIG. 1E shows a view of the tibial component from its second surface.

Referring now to surgical methods (and corresponding instrumentation) which may be used to implant the ankle prosthesis, it is noted that the invention may be utilized, for example, in the context of an anterior approach, a lateral approach, a combined lateral and medial approach, or a combination of a lateral and anteromedial approach.

In any case, referring now to FIGS. 2A-2K, implantation steps of an ankle prosthesis according to an embodiment of the present invention may be as follows:

1) Do a lateral approach, fibular osteotomy and exposure of the joint.
2) Attach two pins to the tibia and one to the medial talus.
3) With use of fluoroscopy, adjust the alignment of the tibia and lock this so that the shaft of the tibia is parallel to the radiopaque rod in the alignment jig.
4) Strap the foot on the clear foot plate.
5) Adjust the cutter pivot assembly to allow a side cutting instrument (e.g., drill) to arc the outer surface of the tibial component from the tibia. This device allows proximal-distal adjustment and anterior/posterior adjustment. A set of pivot guides may be associated with each size of implant, that is, for a small implant there may be a smaller radius of curvature. The guides may also have stops to avoid overreaching with the side cutting bit.
6) After the appropriate amount of bone is remove from the tibia (e.g., enough to allow proper positioning of the foot—with the calcaneus in neutral position) attention is directed to the talar side.
7) The foot plate is positioned so the plantar aspect of the entire foot is perpendicular to the tibia. The translucent plate on which the foot is secured allows the surgeon to be absolutely sure the heel and metatarsals all are in contact.
8) The superior dome of the talus is then side cut with the same pivot guide assembly.
9) Trial spacers are placed to ensure parallelism of the cuts, and no overtensioning of the deltoid.
10) The spacers may have lateral slots for drilling the ridge holes and overhangs through which pins are temporarily placed to secure the guide for the ridge holes.
11) One or two lateral-medial ridge hole(s) are drilled adjacent to the exposed cut surface of the distal tibia and one or two others are drilled in the superior surface of the proximal talus.

12) Trial tibial and talar components are placed and again the deltoid tightness is assessed. If needed more bone is removed with the side cutting instrument (e.g., drill) and pivot guide.

13) Occasionally, the surgeon may make an anteromedial incision to remove bone from the medial side of the joint (the surgeon may decide to use the same implant with a medial and/or lateral overhang to the talar component). The surgeon may also decide to use a cemented polyethylene button on the medial side of the fibula.

14) The lateral side is then adjusted in a superior/inferior direction to maintain ligament tension on the calcaneal-fibular ligament.

15) The lateral fibula is fixated with standard orthopaedic hardware such as a plate and/or screw, tension band technique or intramedullary device.

In another embodiment in connection with step (2) above, the surgeon may have the option of not only placing a pin in the talus but also in the calcaneus.

In another embodiment, step (7) above may be combined with the step (4) above, such that step (4) includes both elements (i.e., strapping the foot on the clear foot plate and positioning the foot plate.

Other embodiments of the present invention may include the following surgical methods and corresponding instrumentation:

1. Anterior Approach

A. Technique

In the anterior approach according to one embodiment a straight incision may be used (e.g., to minimize wound problems). The dissection may be carried through the extensor hallucis longus sheath with the EHL tendon retracted medially and the neurovascular bundle retracted laterally (this leaves the blood supply to the extensor digitorum brevis intact for the possible use in a flap in case of a wound problem).

The tibial bone cut may be made from a cutting block which may be set essentially parallel to the floor when the foot is in a plantigrade position on both the AP view and perpendicular to the midlongitudinal axis of the tibia on the lateral view. Fluoroscopy may be used to determine the position of the cutting block so that a minimal amount of bone will be resected with the proper alignment. In one example (which example is intended to be illustrative and not restrictive) some patients may be treated using a guide system based on the plane of the sole of the foot that will allow cuts to be made parallel to this plane in the tibia and the superior portion of the talus. For the top portion of the talar cut an extension to the tibia cutting block may be used. The front and back or the side cuts may be performed next. For the front and back cuts, a different cutting block may be attached to the talus. For the side cuts, the same cutting block or a third cutting block referenced to the talus may be used. Once the cuts are completed, both the tibia and talar trial components may be placed and range of motion and ligament laxity/tightness determined. Finally, ligament balancing may be performed to help insure proper ligament tension both medially and laterally without excessive laxity or tightness in the ligaments. In another example (which example is intended to be illustrative and not restrictive) instrumentation stops may be available for some or all cuts used and/or appropriate design features may be incorporated to make it difficult to cut beyond a desired range (e.g., in the area of the posterior aspect of the tibia where injury to tendons and nerves are possible; tendon lacerations from such cuts have occurred in total ankle replacements).

B. Instrumentation

The instrumentation may include a cutting block for the distal tibial cut attached to a long rod secured to the proximal leg. This block may be designed to permit fine adjustments superior-inferior, medial lateral, and may have a capture mechanism for the saw blade. The cutting block may be placed under fluoroscopic control. In one example (which example is intended to be illustrative and not restrictive) 2 pins in the tibia may be used for fixation. In this case, the first pin may be placed with consideration of internal-external rotation. Afterward the varus-valgus position may be determined, for example, by fluoroscopic imaging and/or from the plane of the sole of the foot and the second pin may be placed. Next the extension-flexion position for the lateral X-ray image may be determined and when the position of the block permits a cut perpendicular to the mid-longitudinal axis of the tibia the height of the tibial rod may be secured at the level of the proximal tibia. The height of the cut may be fine-tuned at the cutting block. The AP view may be repeated and the medial-lateral extent of the cut may then adjusted and locked in. The saw may have a stop to reduce possibility of injury to vital posterior soft tissue structures. After this cut is made, the talus may be positioned in all three planes and a block extension may be used to remove the superior surface.

The instrumentation may include right and left guides for making the posterior, anterior, and medial/lateral cuts on the talus. In addition, the invention may employ a guide for cutting the corresponding surfaces of the malleoli and placing a slot for the buttons (e.g., poly buttons).

2. Lateral Approach

A. Technique

The advantages of this approach (relative to the anterior approach) may include: 1) less bone resection; 2) essentially complete access to the lateral joint space; 3) ability to perform a controlled release of chronically tight posterior ankle and/or subtalar joint ligaments; 4) decreased risk of tendon and/or nerve lacerations with the ability to place retractors on the posterior tibia; and 5) likely decreased incidence of wound complications. In addition, this lateral approach offers the possibility to perform one or more curved cuts and/or one or more flat cuts close to a curved cut on both of these articular surfaces (i.e., the distal tibial and proximal talar). Such curved cuts and/or one or more flat cuts close to a curved cut may aid in minimizing bone resection, thereby retaining the periankle bone stock (which is a particularly strong bone for stress transfer). Curved or nearly curved surfaces with minimal bone resection should allow for a greater area of coverage of this stronger bone.

To have access to the ankle, the lateral side of the fibula is osteotomized. The distal fibular fragment may be reflected posteriorly, after incising the anterior talofibular ligament (which may be repaired at the end of the procedure). The fibula osteotomy may be later fixed with screws and/or plate and/or other fixation at the end of the procedure. In one example (which example is intended to be illustrative and not restrictive) bone cuts may be made by an oscillating curved saw blade for the curved talar and/or tibial cuts or alternatively flat cuts but with minimal bone resection. These cuts may be aligned by bony landmarks and/or off an alignment guide. K wires may be placed and checked fluoroscopically and used to fix the alignment guides and/or guide the bone cuts. The described approach may give access to the lateral joint surface of the talus and the medial aspect of the lateral malleolus. One or both of these surfaces may be prepared for resurfacing from this approach.

To gain adequate access to the medial joint surface when a transfibular approach is used, a separate incision may be made on the anteromedial side of the ankle joint. Through the anteromedial and lateral incisions any anterior osteophytes may be removed. This approach may allow resurfacing of the medial aspect of the talus, the lateral aspect of the medial malleolus and controlled cutting of the tibia and talus from the lateral side. From the anteromedial incision either an osteotome may be placed along the superior medial gutter into the tibia or pins may be used to block the progress of the saw blade and prevent cutting the medial malleolus when the cuts are made from lateral to medial. If curved cuts are used the extent of the curve anteriorly and posteriorly may likely be slightly more than that of the ankle prosthesis. From the lateral approach one or more small slot cuts for initial fixation of the implant(s) may be made. In one example (which example is intended to be illustrative and not restrictive) these slot cuts(s) may be done with a drill directly through the joint line to simultaneously produce a slot into the tibia and talus. This may correspond to a small peg on the tibial and/or talar trials and/or implants to guide insertion and maintain alignment. From the medial approach, when needed, the surgeon may prepare the medial aspect of the talus and/or the lateral aspect of the medial malleolus for implant fixation.

B. Instrumentation

If curved cuts are to be used, an oscillating saw, drill, bun, and/or router may, in one example (which example is intended to be illustrative and not restrictive), be employed to make such cut(s). On the tibial side, pin(s) may be placed under fluoroscopic guidance to define the plane of the cut. In the AP projection, this pin may be placed to lock in the varus-valgus and internal-external rotation position of the tibial tray. In one example (which example is intended to be illustrative and not restrictive) a cutting saw that is curved with an attached guidance slot for the pin may be used. For positioning of the talar cut a pin may be used perpendicular to the side of the talus or somewhat off this perpendicular according to the alignment of the cone, or the cut may be made off the pin already inserted in the tibia after the talus has been held in the correct amount of varus-valgus and internal-external rotation by the surgical team. For the tibial and talar guides an alignment cutting block may be used. In one example (which example is intended to be illustrative and not restrictive) the cuts for the pegs may be made with the drill, router, or small saw to simultaneously make the slots for the talar and tibial components. This may be done in one of many ways known to those of ordinary skill in the art. Trials with undersized pegs for the slots can then be applied. Trials may be used to judge alignment, adequate range of motion without impingement and ligament tension.

A separate guide for the medial and lateral cuts on the talus may be used to assure proper width of the talus to fit the implant. In one example (which example is intended to be illustrative and not restrictive) it is likely that after the top talar cut, the lateral cut will be made on the talus. A guide on the top of the talar may then be used to make a corresponding medial cut through the anteromedial incision, and lateral cut through the transfibular approach. This may be done in a reverse order. The medial cut may be made as described for the anterior technique. The lateral cut may be made with a cutout along the lateral joint surface (e.g., that is cleared by a side cutting drill bit with a depth stop). The medial surface of the lateral malleolus may be prepared as a standard patellar resurfacing to allow a cemented button (e.g., poly button) to be placed. The lateral surface of the medial malleolus may be prepared with a saw cut and placement of a slot for the button peg.

Figure 3:
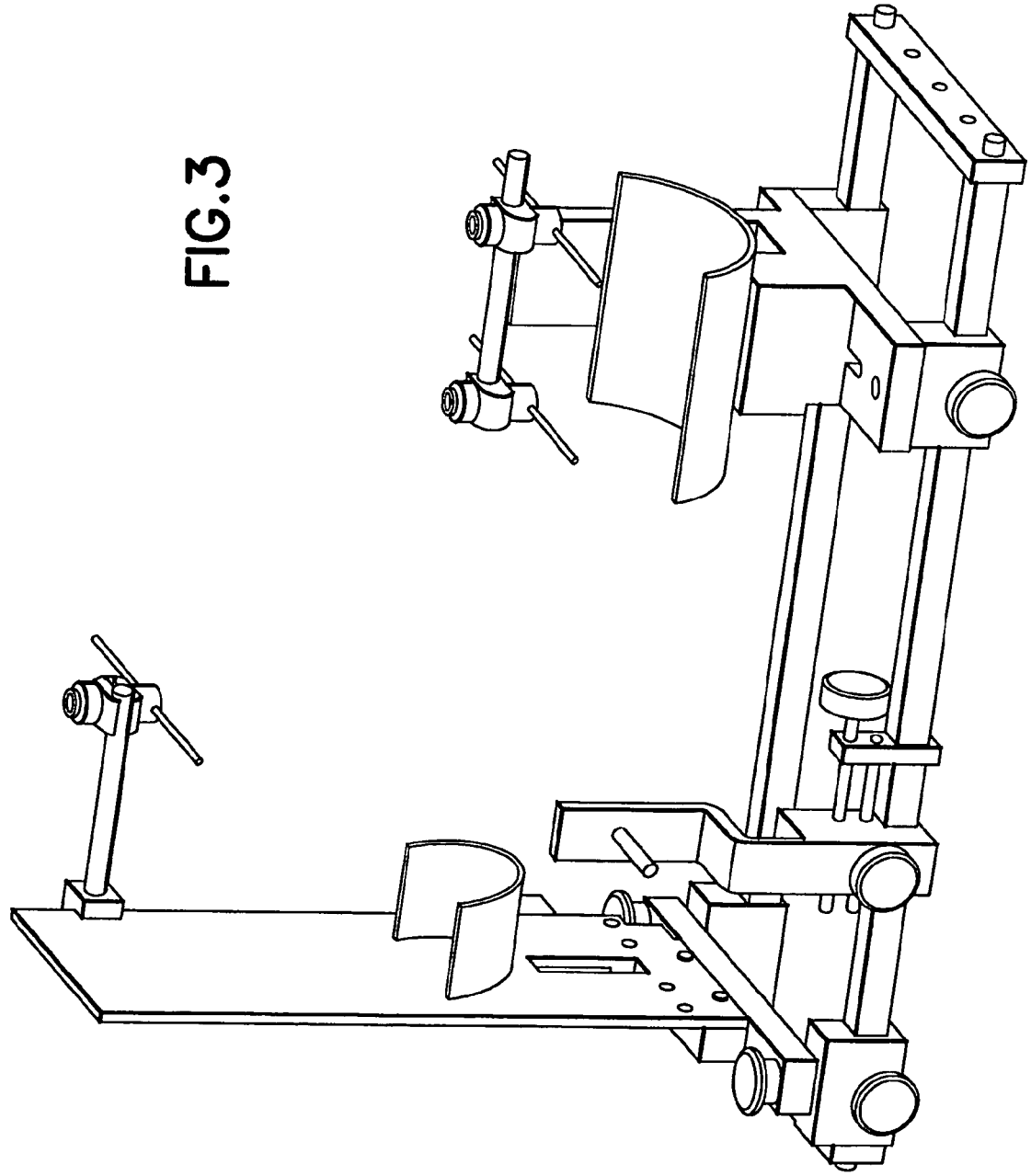
FIG. 3 shows instrumentation according to another embodiment of the present invention.

Referring now to FIG. 3, instrumentation according to another embodiment of the present invention is shown.

In another embodiment the instrumentation may be made to align the cuts according to bony landmarks and/or fluoroscopic control.

In another embodiment the guides for the cutting may be fixed to an external fixator, and/or be fixed directly to the bone, and/or be based on a guidance system (e.g., from the plane of the sole of the foot). The aforementioned configurations may be used for purposes of overall alignment and stability.

In another embodiment some or all of the instrumentation may be made so as to be used on the right and left ankles (i.e., all of the instrumentation may be made so as to be used on the right and left ankles or there may be some separate instrumentation for the right and/or left sides).

In another embodiment an ankle replacement may be shaped to conform to the curvilinear shape of the bones which comprise the ankle.

In another embodiment curved as well as straight cuts may be used to prepare the bony surfaces for implantation (e.g., in order to sacrifice less bone as compared to straight cuts alone).

In another embodiment an ankle replacement may be inserted through a lateral and medial approach (the implant may, of course, be inserted using another approach (e.g., an anterior approach).

In another embodiment revision tibial and talar implants with threaded (e.g., male) fixation peg(s) on the surface facing the bone may be used with a variety of differently sized (e.g., length, width and/or shape) interchangeable (e.g., female) fixation devices.

In another embodiment an ankle replacement may be composed of metal, ceramic, an ultra high molecular weight polyethylene plastic and/or a tantalum mesh.

In another embodiment an ankle prosthesis is provided in which at least one component (e.g., a tibial component) includes a polymer plastic bearing surface (e.g., ultra high molecular weight polyethylene (UHMWPE)), wherein the bearing surface is integrally attached to a metal and/or ceramic backing plate. This plate may contain an appropriate surface for interfacing with and attaching to bone. Further, this interface surface may be of a porous nature to allow bone ingrowth. Further still, malleolar components may be universal. These components may use mechanical attachment with a bone-cement interface and/or an appropriate porous metal backing to allow fixation to the bone.

In another embodiment the polyethylene articular surfaces may be produced by direct compression molding (a process that provides enhanced aging resistance and wear resistance).

In another embodiment a method of attachment between the polyethylene bearing surface and the metal backing may utilize direct compression molding of the articular surface onto the metal backing (with interlocking provided by any of the methods known to those of ordinary skill in the art (e.g., undercuts and/or porous surface penetration).

In another embodiment a system of implant(s) to accommodate the special requirements of revision surgery (and/or conversion to a fusion) is provided. Revision problems such as, for example, subsidence and bone loss, subluxation and possible dislocation may be addressed by this embodiment. In the event such problems should occur (or to revise other total ankle replacements), revision implants may be provided. For dislocation or subluxation the ability to revise the bone cuts so the joint will not sublux may be necessary and provided for. In this instance (as well as the instance of significant bone loss), augmentation of bone stock may be allowed for. The use of bone substitutes and/or bone graft with bone substitutes may be possible. Design features such as metal peg(s) screwed into the revision prosthesis and/or slot(s) and/or fin(s) may be used. These design features may articulate with the patient's bone to assist in fixation (e.g., of the bone graft to the patient's bone and the implant).

In another embodiment the present invention lends itself directly to computer navigational and/or robotic implantation. For example, use of a navigational system may help insure proper alignment of the foot versus the tibia in judging things such as heel valgus and foot position versus the tibia. Further, it is noted that an embodiment of the present invention may require cutting mechanism(s) be attached to the tibia in a way that allows direct (e.g., through the fixator setup) distraction of the joint with the cutting guides attached to the fixator.

In another embodiment, an element of the present invention may be a curved or nearly curved shape on the bone side of the tibial and talar components. These may be curved cuts or nearly so using a series of flats cuts to take minimal bone.

In another embodiment, an element of the present invention may be the external fixating jig for alignment and the tibial and talar bone cuts which are used for the purpose of alignment.

In another embodiment, an element of the present invention may be the fixation of the whole jig to the tibia as well as to the foot.

In another embodiment, the prosthesis may include a medial-lateral ridge.

In another embodiment, the prosthesis may maintain stability with little or no edge evolving.

While a number of embodiments of the present invention have been described, it is understood that these embodiments are illustrative only, and not restrictive, and that many modifications may become apparent to those of ordinary skill in the art. For example, the steps described in connection with the surgical procedures (and/or any assembly/manufacturing) may be carried out in any desired order, some steps may be omitted, and/or other steps may be added. Further, some of the instrumentation described herein may not be utilized and/or additional instrumentation may be employed. Further still, the ankle prosthesis may include left sided and right sided components (e.g., tibial and talar components). Of note, such left sided and right sided components may be used, in one embodiment, due to a conical component of the articular geometry. Further still, the apparatus (and/or its components) may, of course, have any desired dimensions (e.g., for any desired patient—man, woman or child). Further still, the apparatus (and/or its components) may be provided in a "line" or "family" of devices (e.g., small, medium and large; adult, child; male, female). Further still, the apparatus (and/or its components) may be provided in standard sizes.

We claim:

1. A method of implanting an ankle prosthesis in a subject having an ankle joint in need of replacement, the ankle joint including a distal tibia end, a fibula, and a talus, the method comprising:
   providing a fixed-bearing ankle prosthesis comprising a tibial component and a talar component, wherein:
      the tibial component comprises a convex tibial attachment surface defined by a circle arc and a tibial articulating surface;
      the talar component comprises a medial edge, a lateral edge, a concave talar attachment surface defined by a circle arc, and a talar articulating surface, the talar articulating surface directly contactable with the tibial articulating surface;
      the tibial articulating surface comprises a medial concave condylar facet and a lateral concave condylar facet, each condylar facet having a radius of curvature in a medial-lateral plane that defines a respective circle arc, the facets separated from one another by a convex central portion;
      the talar articulating surface comprises a medial convex condyle that underlies the medial condylar facet, and a lateral convex condyle that underlies the lateral condylar facet, the condyles separated from one another by a concave central portion that underlies the tibial convex central portion;
      the medial condyle of the talar component has a first single radius of curvature in the medial-lateral plane that defines a convex circular arc cross-section continuously extending, in the medial-lateral plane, from the medial edge of the talar component to the concave central portion of the talar articulating surface;
      the lateral condyle of the talar component has a second single radius of curvature in the medial-lateral plane that defines a convex circular arc cross-section continuously extending, in the medial-lateral plane, from the lateral edge of the talar component to the concave central portion of the talar component second surface;
      the medial condyle radius of curvature is smaller than the medial condylar facet radius of curvature; and
      the lateral condyle radius of curvature is smaller than the lateral condylar facet radius of curvature;
   performing an osteotomy of the fibula to gain lateral access to the distal tibia end and the talus;
   distracting the ankle joint;
   making a concave cut in the distal tibia end corresponding to the convex curve of the tibial attachment surface to create a tibial cut end;
   making a convex cut in the talus corresponding to the concave curve of the talar attachment surface to create a talar cut end;
   fixing the tibial attachment surface of the tibial component to the tibial cut end;
   fixing the talar attachment surface to the talar component to the talar cut end;
   approximating the respective articulating surfaces of the tibial component and the talar component so that they contact one another; and
   refixating the fibula.

2. The method of claim 1, wherein the talar condyle radii of curvature are between 92% and 96% of the corresponding tibial condylar facet radii of curvature.

3. The method of claim 1, wherein the medial and lateral condylar facets of the tibial component have concave circular arc cross-sections extending in an anterior-posterior direction, the medial and lateral condyles of the talar component have convex circular arc cross-sections extending in the anterior-poster direction, and anterior-posterior radii of the circular arc cross-sections of the tibial component are larger than corresponding radii of the circular arc cross-sections of the talar component.

4. The method of claim 3, wherein the anterior-posterior radii of the circular arc cross-sections of the talar component are between 85% and 96% of the corresponding radii of the circular arc cross-sections of the tibial component.

* * * * *